United States Patent [19]

Ogunbiyi et al.

[11] Patent Number: 4,758,595
[45] Date of Patent: Jul. 19, 1988

[54] DISINFECTING AND PRESERVING SYSTEMS AND METHODS OF USE

[75] Inventors: Lai Ogunbiyi, Fairport; Francis X. Smith, Walworth, both of N.Y.; Thomas M. Riedhammer, Toms River, N.J.

[73] Assignee: Bausch & Lomb Incorporated, Rochester, N.Y.

[21] Appl. No.: 867,405

[22] Filed: May 14, 1986

Related U.S. Application Data

[63] Continuation of Ser. No. 680,450, Dec. 11, 1984, abandoned, which is a continuation-in-part of Ser. No. 655,965, Sep. 28, 1984, abandoned.

[51] Int. Cl.$^4$ ............................................. A61K 31/155
[52] U.S. Cl. ....................................... 514/635; 424/78
[58] Field of Search .......................... 424/78; 514/635

[56] References Cited

U.S. PATENT DOCUMENTS

| | | | |
|---|---|---|---|
| 2,336,605 | 12/1943 | Ernsberger et al. | 167/22 |
| 3,860,729 | 1/1975 | Strandskov et al. | 426/151 |
| 4,022,834 | 5/1977 | Gundersen | 259/564 |
| 4,361,548 | 11/1982 | Smith et al. | 424/78 |
| 4,405,645 | 9/1983 | Rothlizberger et al. | 424/326 |
| 4,499,077 | 2/1985 | Stockel et al. | 424/149 |
| 4,519,803 | 5/1985 | Clare | 8/445 |

FOREIGN PATENT DOCUMENTS 2517208 6/1983 France .
1432345 4/1976 United Kingdom .

*Primary Examiner*—Joseph L. Schofer
*Assistant Examiner*—J. M. Reddick
*Attorney, Agent, or Firm*—Craig E. Larson; Christopher E. Blank; Bernard D. Bogdon

[57] ABSTRACT

A preserving solution comprising a microbicidally or fungicidally effective amount of a biguanide or water-soluble salt thereof, in combination with a buffer system, said biguanide having the formula:

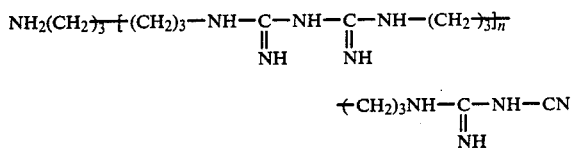

wherein n is from 1 to 500, said biguanide being present in an amount from 0.000001 to 0.0003 weight percent, useful for preserving, for example, a cosmetic formulation.

18 Claims, No Drawings

DISINFECTING AND PRESERVING SYSTEMS AND METHODS OF USE

CROSS-REFERENCE TO A RELATED APPLICATION

This is a continuation of co-pending application Ser. No. 680,450 filed Dec. 11, 1984 now abandoned, which is a continuation-in-part of our copending application, Ser. No. 655,965, filed Sept. 28, 1984 now abandoned.

BACKGROUND OF THE INVENTION

1. Field of the Invention

This invention relates generally to improved disinfecting and/or preserving systems. More specifically, the invention pertains to the use of such systems in solutions for contact lenses and contact lens care.

2. Description of Related Art

Generally, contact lenses in wide use fall into two categories: the hard or rigid corneal type lenses formed from materials prepared by polymerization of acrylic esters, such as polymethyl methacrylate (PMMA), and gel, hydrogel or soft type lenses made of polymerized hydrophilic or hydrophobic monomers, such as 2-hydroxyethyl methacrylate (HEMA). The hard acrylic type contact lenses are characterized by low water vapor diffusion constants, resistance to the effects of light, oxygen and hydrolysis and absorb only minor amounts of aqueous fluids. Because of the durability of hard contact lenses, coupled with their tendency not to absorb appreciable amounts of water, the selection of suitable disinfecting agents, cleaning agents or other lens care compounds is relatively non-critical.

However, unlike hard lenses, soft type contact lenses and certain of the newer gas permeable hard contact lenses have a tendency to bind and concentrate significantly more fluids, environmental pollutants, water impurities as well as antimicrobial agents and other active ingredients commonly found in lens care solutions. In most instances, the low levels of the ingredients in lens care solutions do not lead to eye tissue irritation when used properly. Nevertheless, because of the inherent binding action of protein deposits and soft lens materials disinfecting agents and preservatives tend to build up on lens surfaces and become concentrated to potentially hazardous levels, such that when released can cause corneal inflammation and other eye tissue irritation.

Previous efforts to alleviate the problem of binding and concentrating disinfectants and preservatives onto contact lens surfaces, and reducing the potential for eye tissue irritation have not been totally satisfactory. For example, in spite of low toxicity levels not all disinfectants are compatible for use with all types of contact lenses. Many hard lens disinfecting and preservative solutions contain benzalkonium chloride or chlorobutanol. Although they are effective antibacterial agents, their use can result in a loss of lens hydrophilic properties, cause solution instability or may even lack compatibility with certain types of hard lenses, e.g., high silicon content.

Other antibacterial agents were found to be more compatible with contact lenses and exhibit less binding on lens surfaces. In one case, it was found that chlorhexidine, a biguanide, binds to soft lens material seven times less than benzalkonium chloride, but the presence of proteinaceous oily tear-film deposits can double the amount of chlorhexidine absorbed over that of clean lenses. U.S. Pat. No. 4,354,952 discloses very dilute disinfecting and cleaning solutions containing chlorhexidine or its salts in combination with certain amphoteric and non-ionic surfactants. These solutions were found to reduce the amount of binding of chlorhexidine on hydrophilic soft contact lenses. Notwithstanding the reduction in binding achieved by this invention, the use of chlorhexidine did result in certain tradeoffs. That is, the antimicrobial activity of the chlorhexidine may be diminished when used with certain amphoteric surfactants. Furthermore, if not used inproper ratio, the surfactant and disinfectant will precipitate unless a non-ionic type surfactant is also employed.

U.S. Pat. No. 4,361,548 discloses a contact lens disinfectant and preservative containing dilute aqueous solutions of a polymer; namely, dimethyldiallylammonium chloride (DMDAAC) having molecular weights ranging from about 10,000 to 1,000,000. Amounts of DMDAAC homopolymer as low as 0.00001 percent by weight may be employed when an enhancer, such as thimerosal, sorbic acid or phenylmercuric salt is used therewith. Although lens binding and concomitant eye tissue irritation with DMDAAC were reduced, it was found in some users to be above desirable clinical levels.

British Pat. No. 1,432,345 discloses contact lens disinfecting compositions containing a polymeric biguanide (of the type contemplated by applicants) and a phosphate buffer. The concentration of the disinfecting polymer disclosed by this patent is substantially higher than that of the present invention. The products embraced by this patent have not found acceptance by the consumer. Corneal staining is an indication of patient acceptability and compositions as disclosed by this patent have staining value of 17% or more present, far above that which is desirable for patient acceptability, see Table V in the Examples of this application.

Other efforts to reduce or eliminate soft lens binding have led to the use of anti-binding or detoxifying agents, like polyvinyl pyrrolidone (PVP) and polyvinyl alcohol (PVA). However, these polymers alone were found to be ineffective for the most part, in reducing lens binding and eye tissue irritation.

Accordingly, there is a need for improved disinfecting and preservative solutions which are compatible for use with most types of contact lenses while maintaining both a high level of antibacterial activity and low order of toxicity to eye tissue with little or no binding or concentrating of the disinfecting agent onto lens surfaces.

Accordingly, there is a need for improved preservative systems that maintain a low order of toxicity and irritation to tissue in and surrounding the eye, i.e., the eye itself, the upper eyelid, the lower eyelid, etc.

The present invention provides for improved solutions for disinfecting and/or preserving contact lenses. The solutions are compatible with both hard and soft type lenses, and are adaptable for use with virtually any of the commonly known disinfecting techniques, including "cold" soaking under ambient temperature conditions, as well as with high temperature disinfecting methods. The disinfecting and preservative solutions of the present invention are especially noteworthy for their wide spectrum of bactericidal and fungicidal activity at low concentrations coupled with very low toxicity and reduced affinity for binding and concentrating when used with soft type contact lenses. Our co-pending application, Ser. No. 655,965, filed Sept. 28, 1984, deals more specifically with improved disinfecting and/or preserving solutions for contact lenses and contact lens care.

In addition to solutions for contact lenses, the instant invention provides for improved preservative systems for cosmetic products, specifically intended for those products used near the eyes. The advantage to this preservative system is its wide spectrum of bactericidal and fungicidal activity at low concentrations coupled with very low toxicity and irritation.

SUMMARY OF THE INVENTION

In accordance with this invention, there is provided an aqueous solution for disinfecting and/or preserving items such as contact lenses and cosmetic products comprising microbicidally effective amounts of a biguanide or water-soluble salts thereof having the following general formula:

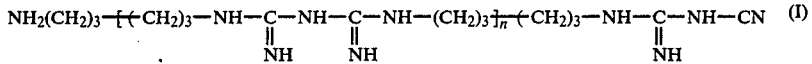

wherein n is from 1 to 500 in combination with a buffer.

DESCRIPTION OF THE PREFERRED EMBODIMENTS

The biguanides for use in the present invention include hexamethylene biguanides, their polymers and water-soluble salts of such base compounds and polymers. Generally, the polymers have molecular weights of up to about 100,000 and are present in amounts from almost 0.000001 to about 0.0003 weight percent. Typically, the solutions will be made isotonic with lacrimal fluids. The antibacterial action of the biguanide-containing solutions described herein may also be supplemented by the addition of other germicidal agents. Because the overall germicidal activity of such combinations will in some instances be greater than when each is used separately, the concentration of total disinfectant in solution can be lowered further reducing the potential for binding, concentrating and adverse toxic reactions.

The disinfecting solutions of the present invention are effective at low concentrations against a wide spectrum of microorganisms, including but not limited to *S. epidermidis*, *C. Albicans*, *A. fumigatus*, etc. The solutions contain as their principal microbicide a biguanide of formula I.

That is to say, the present invention contemplates low molecular weight oligomers where n averages from 4 to 7, high molecular weight long chain polymers up to approximately 100,000 M.W., as well as individual monomers of such polymers where n is 1. In addition to the above, the present invention also includes water-soluble salts of the free bases, such as hydrochloride and borate salts, acetate, gluconate, sulfonate, tartrate and citrate salts. Most conveniently, however, the water-soluble salts, e.g., hydrochloride, of the foregoing biguanides are used in the disinfecting/preservative solutions wherein the value for n generally averages between 2 and 12, and more specifically from 3 to 8. Thus, one preferred group of water-soluble biguanides described herein will have average molecular weights of at least 1,000 and more particularly from 1,000 to 50,000 M.W.

The range of polymeric and monomeric biguanides within the foregoing broad definition for use in the solutions of the present invention is rather surprising and unexpected, since polymers in the higher molecular weight ranges usually demonstrate less binding and lower toxicity levels than corresponding lower molecular weight materials. However, the monomer, e.g., hexamethylene biguanide hydrochloride, provides good bactericidal activity at low concentrations and with little binding effect, as does polyhexamethylene biguanide hydrochloride wherein n averages 4 to 7.

The above-described biguanides and methods of preparation are described in the literature. For example, U.S. Pat. No. 3,428,576 describes the preparation of such biguanides from a diamine and salts thereof and a diamine salt of dicyanimide. This patent expressly teaches methods for making, e.g., the hydrochloride salt of polyhexamethylene biguanide which is also commercially available from ICI Americas, Inc., Wilmington, DE 19897, under the trademark Cosmocil CQ. For convenience purposes only, the biguanides described hereinafter for disinfecting and/or preserving contact lenses shall be referred to as "PHMB."

The preserving solutions of the instant invention are effective in concentrations as low as 0.000001 weight percent PHMB. Generally, the disinfectant and preservative solutions will contain from about 0.00001 to about 0.0003 weight percent (i.e., three parts per million -ppm) PHMB. It has also been found that the bactericidal activity of the solutions may be enhanced or spectrum of activity broadened through the use of a potentiating amount of a second disinfectant or germicidal agent. As a result, the total concentration of disinfectant required when PHMB is used in combination with other germicidal agents may be lowered further due to complementary bactericidal activity, which is most desirable in achieving the lowest possible potential for lens binding, concentrating and particularly skin, eye or eyelid tissue inflammation. Thus, the effective concentration of PHMB may be lowered to about 0.000001 weight percent and up to about 0.0003 weight percent.

The disinfecting/preserving solutions of this invention contain a buffer, preferably a borate buffer, e.g., boric acid, sodium borate, potassium tetraborate, potassium metaborate or mixtures of the same. Applicants were surprised to find that, at the amounts of PHMB present in the solutions of this invention, a borate buffer system was exceptionally effective. This is particularly surprising in view of British Pat. No. 1,432,345 disclosing phosphate buffers for solutions containing higher amounts of PHMB. Whatever the reasons, PHMB solutions buffered only with phosphate are ineffective under the conditions of this invention, see Table I of the examples below.

Applicants have additionally found to their surprise that conventional buffers can be useful in this invention when those buffers are only used in conjunction with increased, but within concentrations of this invention, amounts of PHMB, an increased amount of sequestering agent, an amphoteric surfactant, a non-ionic surfactant or a cationic surfactant. The buffers in this category are sodium or potassium citrate, citric acid, sodium bicarbonate and various mixed phosphate buffers, including combinations of $Na_2HPO_4$, $NaH_2PO_4$ and $KH_2PO_4$. Generally, buffers may be used in amounts ranging from about 0.05 to about 2.5 percent, and more preferably, from about 0.1 to about 1.5 percent (w/w). Suitable sequestering agents include ethylene diaminetetraacetic acid (EDTA), gluconic acid, citric acid, tartaric acid and their salts; e.g., sodium. The foregoing surfactants, when employed as a buffer enhancer will be present in an amount from 0.0001 percent to 5.0 percent (w/w). Additionally, the nonionic surfactant can be employed both as a buffer enhancer and as a cleaning agent or a combined cleaner and disinfecting/preserving solution.

The amphoteric charged surfactant molecule consists of a relatively complex organic portion with a net positive or negative charge. The latter charge is balanced by a positive or negative counterion; (e.g., Na+, Cl−) which is not connected to the molecule by a covalent bond but is held in its environment by the attraction between the oppositely charged moieties. In the amphoteric molecule, the complex organic portion referred to above contains both positive and negative charges (at least one of each). As with the singly-charged molecule, electrical neutrality is provided by counterions, both negative and positive counterions being required for the same molecule. The uncharged portion of the amphoteric molecule contains hydrophobic groups (the charged portions usually function as a part of the hydrophilic groups) and may contain non-charged (i.e. nonionic) hydrophilic groups.

A preferred amphoteric surfactant molecule of this invention is illustrated by the following chemical structures:

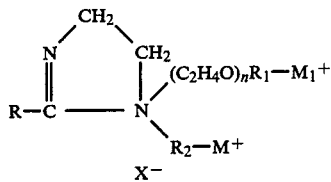

The structure is illustrated in the ionized form as it exists in aqueous media. In this structure, R represents a fatty acid radical of $C_6$–$C_{18}$, e.g., coconut oil which is a mixture of lauric, myristic, oleic, stearic, palmitic and other similar acids; lauric acid; capric acid; caprylic and ethylhexoic acid; oleic acid; linoleic acid and stearic acid; $R_2$ is

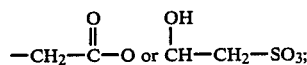

M and $M_1$ are cation salt forming groups, such as hydrogen or alkali metals, X is OH, or the acid group of an anionic surface active agent, e.g., sodium lauryl sulfate or sodium lauryl sulfonate, $R_1$ is H or

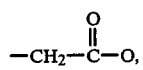

provided, however, when $R_1$ is hydrogen, $M_1$ is absent and n is an integer from 1 to 40. Materials of this type are offered commercially from the Miranol Chemical Co., Doyton, NJ 08810 under the trade name "Miranol." Typical examples of ionized amphoteric salts (commercial trade names Miranol 2MCA and C2M respectively) are shown below:

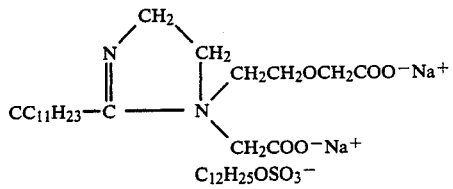

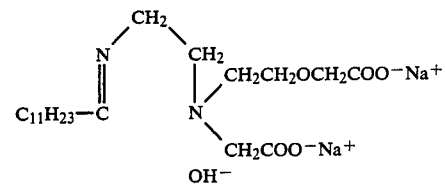

Broadly, these compounds can be monocarboxylate, dicarboxylates or sulfonates. The counterions in the first example are Na+ and $CH_{12}H_{25}OSO_3-$ and in the second example Na+ and OH−.

Another class of amphoteric surfactants is given by the following chemical structure in the ionized form:

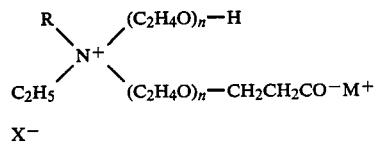

where R is a hydrophobe radical such as methyl octadecyl, methyldodecyl, methyloctadecenyl, etc.; M is an alkali metal, such as Na, K, etc.; X is the negative part of an agent, such as $CH_3OSO_3$, $C_2H_5OSO_3$, Cl, Br, etc.; n is an integer from 1 to 40. Materials of this type are available commercially from Armstrong Chemical Co., Inc., Janesville, WI 53545 under the trade name Sanac. This molecule has a nonionic functionality, $(C_2H_4O)_nH$. Specific examples are [2-(2-carboxyethyl) ethyl] [2-(2-hydroxyethyl)ethyl]methyloctadecylammonium methyl sulfate, potassium salt; [2-(2- carboxyethyoxy) ethyl] [2-(2-hydroxyethoxy) ethyl] methyloctadecenylammonium methyl sulfate, potassium salt; and [2-(2- carboxyethyoxy) ethyl] [2-(-hydroxyethoxy) ethyl] methylododecylammonium methyl sulfate, potassium salt.

Another class of amphoteric surfactants may be exemplified by the following chemical structure, in the ionized form:

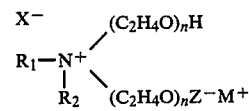

where $R_1$ is a fatty acid radical or other hydrophobe radical, $R_2$ is an alkyl or substituted alkyl radical, Z is a sulfate or sulfonic group, e.g., $-SO_4$, $-CH_2CH_2SO_3$; M is an alkali metal such as Na or K, X is the negative radical from a quaternizing reagent such as $CH_3OSO_3$, $C_2H_5OSO_3$, Cl, Br, etc.

Yet another class of amphoteric surfactants may be exemplified by the following chemical structure in the ionized form:

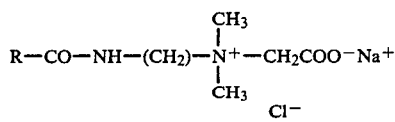

where R is alkylene having 12 to 13 atoms and R—CO— taken together as the acid radical such as coconut acid. Materials of this type are exemplified by cocoamidopropyl betaine commercially available from Stephen Chemical Co., Northfield, IL 60093 under the trade name Amphosol CA.

As suitable cationic surfactants, dual quaternary ammonium compositions are described in U.S. Pat. Nos. 3,525,793 and 3,472,939 and are commercially available from Onyx Chemical Company, Jersey City, N.J. under the trademark BTC 2125M.

The second disinfectant/germicide can be employed as a solution preservative, but it may also function to potentiate, complement or broaden the spectrum of microbicidal activity of PHMB. This includes microbicidally effective amounts of germicides which are compatible with and do not precipitate in the presence of PHMB, and comprises concentrations ranging from about 0.00001 to about 0.5 weight percent, and more preferably, from about 0.0001 to about 0.1 weight percent. Suitable complementary germicidal agents include, but are not limited to thimerosal, sorbic acid, 1,5-pentanediol, alkyl triethanolamines, phenylmercuric salts, e.g., nitrate, borate, acetate, chloride and mixtures thereof. Other germicidal compounds and salts may be used. Suitable salts are soluble in water at ambient temperature to the extent of at least 0.5 weight percent. These salts include the gluconate, isothionate (2-hydroxyethanesulfonate), formate, acetate, glutamate, succinanate, monodiglycollate, dimethanesulfonate, lactate, diisobutyrate and glucoheptonate.

Further embodiments of potentiating or complementary disinfecting agents for use with PHMB also include certain quaternary ammonium compounds which possess a generally wide spectrum of bactericidal activity and wetting properties. Representative examples of the quaternary ammonium compounds are compositions comprised of balanced mixtures of n-alkyl dimethyl benzyl ammonium chlorides.

The aqueous solutions of the present invention when used for treating contact lenses are also adjusted with tonicity agents to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

The aqueous isotonic solutions of PHMB with optional germicidal agents are useful disinfectants for both hard and soft contact lenses without any further additives. Nevertheless, the solutions of the present invention may be formulated into specific contact lens care products, such as wetting solutions, soaking solutions, cleaning and conditioning solutions, as well as all purpose type lens care solutions, etc. and mixtures thereof. Such additives make the solutions more acceptable to the user in terms of greater comfort. However, the additives must be non-toxic and compatible with contact lenses.

When used, neutral or non-ionic surfactants impart cleaning and conditioning properties and are usually present in amounts up to 15 weight percent. The surfactant should be soluble in the lens care solution, non-irritating to eye tissues and still usually have a hydrophilic-lipophile balance (HLB) of 12.4 to 18.8. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available from ICI Americas Inc., Wilmington, DE 19897 under the trademark Tween 20), polyoxyethylene (23) lauryl ether (Brij ® 35), polyoxyethylene (40) stearate (Myrj ® 52), polyoxyethylene (25) propylene glycol stearate (Atlas ® G 2612). Brij ® 35, Myrj ® 52 and Atlas ® G 2612 are trademarks of, and are commercially available from, ICI Americas Inc., Wilmington, DE 19897.

One non-ionic surfactant in particular, consisting of a poly (oxypropylene) -poly (oxyethylene) adduct of ethylene diamine having a molecular weight from about 7,500 to about 27,000 wherein at least 40 weight percent of said adduct is poly (oxyethylene), has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is polyoxamine. Such surfactants are available from BASF Wyandotte Corp., Wyandotte, Mich., under the registered trademark "Tetronic." An analogous series of surfactants is the poloxamer series which is a polyoxyethylene, polyoxypropylene block polymers available from BASF Wyandotte Corp., Parsippany, NJ 07054 under the trademark "Pluronic."

Oher amphoteric, cationic and nonionic surfactants suitable for in the invention can be readily ascertained, in view of the foregoing description, from McCutcheon's Detergents and Emulsifiers, North American Edition, McCutcheon Division, MC Publishing Co., Glen Rock, NJ 07452.

It may also be desirable to include water-soluble viscosity builders in the PHMB-containing solutions of the present invention. Because of their demulcent effect, viscosity buildiers have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose and the like. Such viscosity builders may be employed in amounts ranging from about 0.01 to about 4.0 weight percent or less.

This invention relates to disinfecting and/or preserving solutions for use with most contact lenses, including hard and soft lenses, as well as the newer hard gas permeable type contact lenses, such as described in U.S. Pat. No. 4,327,203. The term "soft contact lens" as used herein generally refers to those contact lenses which readily flex under small amounts of force and return to their original shape when that force is released. Typically, soft contact lenses are formulated from poly (hydroxyethyl methacrylate) which has been, in the preferred formulations, crosslinked with ethylene glycol dimethacrylate. For convenience, this polymer is generally known as PHEMA. Soft contact lenses are also made from silicon polymers crosslinked, for example, with dimethyl polysiloxane. Convention "hard contact lenses," which cover only the cornea of the eye, usually consist of poly (methyl methacrylate) crosslinked with ethylene glycol dimethacrylate.

The aqueous PHMB-containing solutions can be effectively used in disinfecting contact lenses by any of the well recognized methods. For example, lenses may be treated by the "cold" soaking method at room temperature for a period ranging from 4 to 12 hours. The lenses are then removed from the solution, washed in preserved isotonic saline solution and then replaced on the eye.

In addition to the cold soaking method, the solutions disclosed herein are adaptable for use in other types of equipment, such as ultrasonic cleaners. Because the solutions are also stable when heated, they are adaptable for use with high temperature disinfecting methods. Typically, lenses are heated to 80° in a disinfecting unit containing the solution for a time period of at least ten minutes, removed and rinsed with isotonic saline.

In addition, the present invention contemplates the use of the PHMD buffer preservative system in ophthalmologic products and dermatologic formulations applied near the eye. Such use will, of course, depend upon the compatibility of the preservative system with the active ingredient(s) in the product.

The following examples demonstrate the compositions and methods of the instant invention. However, it is to be understood that these examples are for illustrative purposes only and do not purport to be wholly definitive as to conditions and scope of this invention.

EXAMPLE I

An aqueous contact lens disinfectant solution is prepared having the following formulation:

|  | Percent (w/v) |
| --- | --- |
| Polyhexamethylene Biguanide HCl* | .0001 |
| Poloxamine 1107** | .5 |
| Na$_2$EDTA | .011 |
| Boric Acid | 1.10 |
| Sodium Borate | .40 |
| Sodium Chloride | .30 |
| Distilled Water qs | 100.0 |

*n = 4.5 to 6.5
**Flake grade, molecular weight 14,500, 70% (wt.), Tetronic ® 1107, a poly (oxypropylene) - poly (oxyethylene) block co-polymer adduct of ethylene diamine, a trademark of BASF Wyandotte Corp., Wyandotte, MI.

The solution is prepared by gradually heating 80 percent of the water to 80° C. while dissolving the disodium EDTA therein. The boric acid and sodium borate are added to the heated solution of disodium EDTA and dissolved. The sodium chloride is then added to the solution and dissolved, followed by the addition of surfactants. After the solution is cooled to room temperature, the polyhexamethylene biguanide is added, followed by the balance of distilled water. The solution is sterilized by forcing through an 0.22 micron cellulose acetate filter by means of a peristaltic pump and packaged in sterilized plastic containers.

The bactericidal activity of the above solution is tested by exposing *S. epidermidis* (1.6×10$^6$ microorganisms/ml) and *C. albicans* (1.1×10$^6$ microorganisms/ml) each to 20 ml of said solution at room temperature for 5 hours. Subsequently, an aliquot sample of each is placed on an agar plate and incubated for 48 hours at elevated temperatures. At the conclusion of the incubation period, the plates are examined for the development of colonies. The results showed 6 log reduction of *S. epidermidis* microorganisms and 1.3 log reduction of *C. albicans* microorganisms.

EXAMPLE II

An aqueous contact lens disinfecting solution is prepared with the following formulation:

|  | Percent (w/v) |
| --- | --- |
| Polyhexamethylene Biguanide HCl* | .0001 |
| Na$_2$ EDTA | .11 |
| Boric Acid | 1.1 |
| Sodium Borate | .40 |
| Sodium Chloride | .30 |
| Distilled Water qs | 100.0 |

*n = 4.5 to 5.6

The above formulation may be prepared by the method described in Example I.

EXAMPLE III

An aqueous contact lens disinfecting solution is prepared with the following formulation:

|  | Percent (w/v) |
| --- | --- |
| Polyhexamethylene Biguanide HCl* | .00009 |
| Poloxamine 1107 | .5 |
| Na$_2$ EDTA | .11 |
| Boric Acid | .64 |
| Sodium Borate | .16 |
| Sodium Chloride | .49 |
| Distilled Water qs | 100.0 |

*n = 500

The above formulation may be prepared by the method described in Example I.

EXAMPLE IV

An aqueous contact lens disinfecting solution is prepared with the following formulation:

|  | Percent (w/v) |
| --- | --- |
| Polyhexamethylene Biguanide HCl* | .00009 |
| Na$_2$ EDTA | .11 |
| Boric Acid | .64 |
| Sodium Borate | .16 |
| Sodium Chloride | .49 |
| Distilled Water qs | 100.0 |

*n = 50

The solution is prepared by dissolving the sodium borate in approximately 80 percent of the distilled water. The disodium EDTA is then added to the sodium borate solution, followed by dissolving the boric acid and sodium chloride therein. The polyhexamethylene biguanide is added, followed by the balance of distilled water. The solution may be sterilized according to the method described in Example I.

EXAMPLE V

In this example, the effectiveness of polyhexamethylene biguanide hydrochloride (n=4.5 to 6.5) as a preserving agent is evaluated, using (1) a borate buffer system and (2) a phosphate buffer system. Each preserved solution is prepared by the method of Example I and each is adjusted so as to be isotonic. All ingredients are by weight percent unless otherwise noted. Following the microbial test methods of Example I, each solution is evaluated for preservative effectiveness against *S. aureus*, *P. aeruginosa* and *E. coli* organisms after 14 and after 28 days. To be considered effective in this test, there must be at least 3 log reduction in number of organisms for each type of organism at 14 days and at 28 days. The solutions and test results are tabulated in Table I (Solutions) and Table IA (Results) below.

TABLE I

PHMB PRESERVED SOLUTIONS

FORMULATION[1]

| Sol. # | Boric Acid | Sodium Borate | Sodium Chloride | Na$_2$ EDTA | (PPM) PHMB | Dibasic Phosphate | Monobasic Phosphate |
|---|---|---|---|---|---|---|---|
| 1  | 1.1% | 0.40% | 0.30% | 0.11% | 0.99 | — | — |
| 2  | 1.1% | 0.40% | 0.30% | 0.11% | 0.88 | — | — |
| 3  | 1.1% | 0.40% | 0.30% | 0.11% | 0.77 | — | — |
| 4  | 1.1% | 0.40% | 0.30% | 0.11% | 0.66 | — | — |
| 5  | 1.1% | 0.40% | 0.30% | 0.11% | 0.55 | — | — |
| 6  | 1.1% | 0.40% | 0.30% | 0.11% | 0.44 | — | — |
| 7  | 1.1% | 0.40% | 0.30% | 0.11% | 0.33 | — | — |
| 8  | 1.1% | 0.40% | 0.30% | 0.11% | 0.22 | — | — |
| 9  | 1.1% | 0.40% | 0.30% | 0.11% | 0.11 | — | — |
| 10 | 1.1% | 0.40% | 0.30% | 0.11% | 0.05 | — | — |
| 11 | — | — | 0.55% | 0.11% | 0.99 | 0.65% | 0.1% |
| 12 | — | — | 0.55% | 0.11% | 0.88 | 0.65% | 0.1% |
| 13 | — | — | 0.55% | 0.11% | 0.77 | 0.65% | 0.1% |
| 14 | — | — | 0.55% | 0.11% | 0.66 | 0.65% | 0.1% |
| 15 | — | — | 0.55% | 0.11% | 0.55 | 0.65% | 0.1% |
| 16 | — | — | 0.55% | 0.11% | 0.44 | 0.65% | 0.1% |
| 17 | — | — | 0.55% | 0.11% | 0.33 | 0.65% | 0.1% |
| 18 | — | — | 0.55% | 0.11% | 0.22 | 0.65% | 0.1% |
| 19 | — | — | 0.55% | 0.11% | 0.11 | 0.65% | 0.1% |
| 20 | — | — | 0.55% | 0.11% | 0.05 | 0.65% | 0.1% |

Note:
[1]Distilled Water up to 100.0.

TABLE IA

RESULTS
ORGANISM LOG REDUCTION[1]

| Sol. # | S. aureus T = 14 | S. aureus T = 28 | P. aeruginosa T = 14 | P. aeruginosa T = 28 | E. coli T = 14 | E. coli T = 28 | Effective |
|---|---|---|---|---|---|---|---|
| 1  | 6.5 | 5.4 | 6.5 | 5.4 | 6.2 | 5.0 | Pass |
| 2  | 6.5 | 5.4 | 6.5 | 5.4 | 6.2 | 5.0 | Pass |
| 3  | 6.5 | 5.4 | 6.5 | 5.4 | 6.2 | 5.0 | Pass |
| 4  | 6.5 | 5.4 | 6.5 | 5.4 | 6.2 | 5.0 | Pass |
| 5  | 6.5 | 5.4 | 6.5 | 5.4 | 6.2 | 5.0 | Pass |
| 6  | 6.5 | 5.4 | 6.5 | 5.4 | 6.2 | 5.0 | Pass |
| 7  | 6.5 | 5.4 | 6.5 | 5.4 | 6.2 | 5.0 | Pass |
| 8  | 6.5 | 5.4 | 6.5 | 5.4 | 4.7 | 5.0 | Pass |
| 9  | 6.5 | 5.4 | 6.5 | 5.4 | 4.4 | 5.0 | Pass |
| 10 | 6.5 | 5.4 | 6.5 | 5.4 | 4.3 | 5.0 | Pass |
| 11 | 6.5 | 5.4 | 1.5 | 1.9 | 6.2 | 5.0 | Fail |
| 12 | 6.5 | 5.4 | 1.1 | 1.3 | 4.2 | 3.7 | Fail |
| 13 | 6.5 | 5.4 | 0.6 | 0.7 | 3.6 | 1.4 | Fail |
| 14 | 6.5 | 5.4 | 0.6 | 0.3 | 3.3 | 1.6 | Fail |
| 15 | 6.5 | 5.4 | 0.4 | 0.1 | 1.7 | 1.5 | Fail |
| 16 | 6.5 | 5.4 | 0.3 | 0.3 | 1.0 | 1.2 | Fail |
| 17 | 6.5 | 5.4 | 0.3 | 0.3 | 0.4 | 0.7 | Fail |
| 18 | 6.5 | 5.4 | 0.1 | 0.3 | 1.0 | 1.6 | Fail |
| 19 | 6.5 | 5.4 | 0.2 | 0.4 | 1.6 | 3.2 | Fail |
| 20 | 6.5 | 5.4 | 0.1 | 0.5 | 1.5 | 3.3 | Fail |

Note:
[1]3 log reduction at 14 days and 28 days required for each test organisms.

The borate buffered PHMB solutions evaluated are effective as preserved solutions whereas the phosphate buffered solutions are not effective at the PHMB concentrations of 0.99 ppm or less.

EXAMPLE VI

In this example the effectiveness of polyhexamethylene biguanide hydrochloride (n=4.5 to 6.5) as a disinfecting agent is evaluated. Each disinfecting solution is prepared by the method of Example I. All ingredients are by weight percent unless otherwise noted. Following the microbial test methods of Example I, each solution is evaluated as a disinfectant against *S. epidermidis*, and *C. albicans*, and *A. fumigatus* organisms after 5 hours. To be considered effective in this test, there must be at least 3 log ($10^3$) reduction in the amount of *S. epidermidis* and no growth in *C. albicans* within 5 hours. The solutions and test results are tabulated in Table II below.

TABLE II

PHMB DISINFECTING SOLUTIONS

| | FORMULATION[1] | | | | | | ORGANISM LOG REDUCTION | |
|---|---|---|---|---|---|---|---|---|
| Sol. # | Sodium Chlor. | Boric Acid | Sodium Borate | Na$_2$ EDTA | Poloxamine 1107 | PHMB (ppm) | S. epidermidis T = 5 Hrs.[2] | C. albicans T = 5 Hrs.[3] |
| 1  | 0.49 | 0.64 | 0.16 | 0.11  | 0.5 | 0.88 | 6.0 | 1.3 |
| 2  | 0.29 | 1.0  | 0.29 | 0.11  | 0.5 | 0.88 | 6.0 | 1.4 |
| 3  | 0.49 | 0.64 | 0.16 | 0.11  | 1.0 | 0.88 | 6.0 | 1.5 |
| 4  | 0.29 | 1.0  | 0.29 | 0.11  | 1.0 | 0.88 | 6.0 | 1.9 |
| 5  | 0.49 | 0.64 | 0.16 | 0.11  | 0.5 | 0.99 | 6.0 | 1.5 |
| 6  | 0.29 | 1.0  | 0.29 | 0.11  | 0.5 | 0.99 | 6.0 | 1.7 |
| 7  | 0.49 | 0.64 | 0.16 | 0.11  | 1.0 | 0.99 | 6.0 | 1.5 |
| 8  | 0.29 | 1.0  | 0.29 | 0.11  | 1.0 | 0.99 | 4.6 | 2.0 |
| 9  | 0.29 | 1.0  | 0.29 | 0.11  | 0.5 | 0.55 | 4.7 | 0.4 |
| 10 | 0.49 | 0.64 | 0.16 | 0.11  | 1.0 | 0.55 | 4.2 | 0.4 |
| 11 | 0.49 | 0.64 | 0.16 | 0.11  | 1.0 | 0.55 | 3.7 | 1.9 |
| 12 | 0.49 | 0.64 | 0.12 | 0.055 | 1.0 | 0.55 | 4.4 | 2.4 |
| 13 | 0.49 | 0.64 | 0.12 | 0.022 | 1.0 | 0.55 | 4.0 | 2.9 |
| 14 | 0.49 | 0.68 | 0.12 | 0.01  | 1.0 | 0.55 | 4.3 | 4.2 |

Note:
[1]Distilled water qs to 100.0
[2]3 log reduction at 5 hours required.
[3]An indication of log reduction in 5 hours required.

EXAMPLE IX

An aqueous contact lens disinfecting solution is prepared with the following formulation:

| | Percent (w/v) |
|---|---|
| Polyhexamethylene Biguanide HCl* | .00011 |
| Poloxamine 1107 | .50 |

-continued

| | Percent (w/v) |
|---|---|
| Sodium Borate | .20 |
| Boric Acid | .60 |
| Sodium Chloride | .49 |
| Distilled Water qs | 100.0 |

*n = 4.5 to 6.5.

The solution is prepared and sterilized following the procedures of Example I. Additional solutions are prepared in the same manner except the level of PHMB is 2 ppm, 3 ppm, 5 ppm, 10 ppm, or 55 ppm.

The corneal staining property of each of the above solutions is evaluated in small patient clinical groups. The eyes of each patient are examined early in the morning to establish a baseline condition. Then the solution to be evaluated is administered to the patient's eyes. The eyes are observed immediately after application of the solution, four hours later and eight hours later. The increase in corneal staining (redness) is noted for each patient. The limit for acceptable amount of increase in corneal staining is 11 percent. The results are tabulated in Table V below.

TABLE V

| Amount PHMB (ppm) | Percent Corneal Staining (Average for Group) |
|---|---|
| 1 | 7 |
| 2 | 5.5 |
| 3 | 9 |
| 5 | 17 |
| 10 | 21.5 |
| 55 | 62 |
| Controls: Commercial Product (with thimerosal) | |
| F | 35 |
| C* | 25 |

*To date, this commercial product has been considered the best commercial disinfecting solution.

Table IV, in combination with Table V, demonstrates that cytotoxicity and corneal staining are relatively independent functions. A contact lens solution may be non-cytotoxic and still not be acceptable to the patient. However, a contact lens solution which is cytotoxic will definitely be unacceptable to the patient as is the case of using 100 ppm chlorhexidine and BAK in contact lens solutions. On the other hand, 10 ppm PHMB is non-cytotoxic but has an unacceptable level of ocular irritation manifested in clinically observed ocular staining of 21.5 percent. The same explanation applies to 5 ppm PHMB, 10 ppm chlorhexidine and 10 ppm BAK.

EXAMPLE X

In this example, the effectiveness of polyhexamethylene biguanide hydrochloride (n=4.5 to 6.5) as a preserving agent is evaluated, using an enhanced phospate buffer system. Each preserved solution is prepared by the method of Example V and each is adjusted so as to be isotonic. All ingredients are by weight percent unless otherwise noted. Following the microbial test methods of Example I, each solution is evaluated for effectiveness against S. aureus, P. aeruginosa and E. coli organisms after 14 days and after 28 days. To be considered effective in this test, there must be at least 3 log reduction in number of organisms for each type of organism at 14 days and at 28 days. The solutions and test results are tabulated in Tables VI (formulations) and VI-A (results) below.

TABLE VI

| | (FORMULATIONS) | | | | | | |
|---|---|---|---|---|---|---|---|
| | SOLUTIONS | | | | | | |
| Ingredient | 1 | 2 | 3 | 4 | 5 | 6 | 7 |
| Polyvinyl Alcohol (98%) | 1.0 | 1.0 | 1.0 | 1.0 | 1.0 | 1.0 | 1.0 |
| Hydroxypropylmethyl Cellulose | 0.20 | 0.36 | 0.10 | 0.30 | 0.30 | 0.30 | 0.30 |
| Gelatin | 0.10 | 0.10 | 0.10 | 0.10 | 0.10 | 0.10 | 0.10 |
| Dibasic Phosphate | 0.45 | 0.45 | 0.45 | 0.45 | 0.45 | 0.45 | 0.45 |
| Monobasic Phosphate | 0.10 | 0.10 | 0.10 | 0.10 | 0.10 | 0.10 | 0.10 |
| Na$_2$ EDTA | 0.11 | 0.11 | 0.11 | 0.11 | 0.11 | 0.11 | 0.11 |
| Sodium Chlorate | 0.61 | 0.56 | 0.56 | 0.56 | 0.56 | 0.56 | 0.56 |
| PHMD | 1.1 | 1.1 | 1.1 | 1.1 | 1.1 | 1.1 | 1.1 |
| Poloxamine 1107 | — | — | — | — | — | — | 0.10 |
| Cocoamidopropyl Betaine | — | — | — | 0.10 | 0.10 | 0.10 | 0.10 |
| Water, qs to 100.0 | | | | | | | |

TABLE VI-A

| | (RESULTS) | | | | | |
|---|---|---|---|---|---|---|
| | ORGANISM LOG REDUCTION[1] | | | | | |
| Solution | S. aureus | | P. aeruginosa | | E. coli | |
| No. | T = 14 | T = 29 | T = 14 | T = 28 | T = 14 | T = 28 |
| 1 | 4.7 | 2.9 | 1.4 | 1.3 | 5.9 | 4.9 |
| 2 | 4.8 | 5.2 | 1.6 | 1.3 | 5.9 | 4.9 |
| 3 | 5.0 | 5.2 | 1.6 | 1.2 | 5.9 | 4.9 |
| 4 | 6.2 | 5.1 | 5.7 | 4.6 | 6.0 | 5.0 |
| 5 | 6.2 | 5.1 | 5.7 | 4.8 | 6.0 | 5.0 |
| 6 | 6.2 | 5.1 | 5.7 | 4.8 | 6.0 | 5.0 |
| 7 | 6.2 | 5.1 | 5.7 | 4.8 | 6.0 | 5.0 |

[1]3 log reduction at 14 and 28 days required for each test organism.

Solutions 1-3 illustrative of compositions disclosed or suggested by related art discussed at the beginning of this application are ineffective compositions. Four and five are enhanced with a surfactant; compositions six and seven are enhanced with two surfactants according to this invention. Compositions four through seven each have organism log reduction values greater than 3 and are effective.

While the invention has been described in conjunction with specific examples thereof, this is illustrative only. Accordingly, many alternatives, modifications and variations will be apparent to those skilled in the art in light of the foregoing description and it is, therefore, intended to embrace all such alternatives, modifications and variations as to fall within the spirit and broad scope of the appended claims.

What is claimed is:

1. A solution comprising a microbicidally or fungicidally effective amount of a biguanide or water-soluble salt thereof, in combination with a borate buffer system, said biguanide having the formula:

$$NH_2(CH_2)_3\!\!-\!\![(CH_2)_3\!-\!NH\!-\!\underset{\underset{NH}{\|}}{C}\!-\!NH\!-\!\underset{\underset{NH}{\|}}{C}\!-\!NH\!-\!(CH_2)_3]_n\!\!-$$

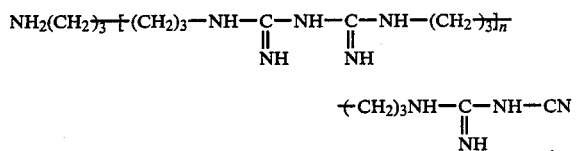

wherein n is from 1 to 500, said biguanide being present in an amount from 0.000001 to 0.0003 weight percent.

2. The solution of claim 1 wherein the biguanide is a polymeric water-soluble salt.

3. The solution of claim 2 wherein the biguanide is a water-soluble salt of polyhexamethylene biguanide.

4. The solution of claim 1 wherein the biguanide is a water-soluble monomer.

5. The solution of claim 2 wherein the biguanide is a polymer having molecular weights under 100,000.

6. The solution of claim 5 wherein the biguanide is a polymer having molecular weights in the range from 1,000 to 50,000.

7. The solution of claim 5 wherein n of the biguanide polymer averages between 2 and 12.

8. The solution of claim 3 wherein n averages from 4 to 7.

9. The solution of claim 3 containing at least 0.00001 weight percent of the biguanide polymer.

10. The solution of claim 9 wherein the biguanide polymer is present in an amount from about 0.0001 to about 0.0003 weight percent.

11. The solution of claim 1 containing microbicidally effective mixtures of a biguanide or water-soluble salt thereof and at least one other germicidal agent.

12. The solution of claim 2 wherein the biguanide is a water-soluble salt of polyhexamethylene biguanide wherein n averages between 2 and 12.

13. A solution according to claim 3 wherein the biguanide is effective to preserve the solution against *S. aureus, P. aeruginosa* and *E. coli organisms.*

14. A solution according to claim 3 which is effective as a disinfecting solution against *S. epidermis* and *C. albicans* organisms.

15. A solution according to claim 1 in which the biguanide is a preservative for the solution.

16. An aqueous solution according to claim 15.

17. A solution according to claim 15 in which the solution is an aqueous solution for contact lens care and contains additionally at least one component from the group consisting of amphoteric, nonionic and cationic surfactants, tonicity agents, sequestering agents and viscosity builders.

18. A solution according to claim 1 in which the solution is an aqueous solution for disinfecting contact lenses and contains additionally at least one component from the group consisting of amphoteric, nonionic and cationic surfactants, tonicity agents, sequestering agents and viscosity builders.

* * * * *